United States Patent [19]
Geoghegan et al.

[11] Patent Number: 4,891,230
[45] Date of Patent: Jan. 2, 1990

[54] DILTIAZEM FORMULATION

[75] Inventors: Edward J. Geoghegan, Athlone, Ireland; Seamus Mulligan, Gainesville, Ga.; Donald E. Panoz, Tuckerstown, Bermuda

[73] Assignee: Elan Corporation plc, Athlone, Ireland

[21] Appl. No.: 120,952

[22] Filed: Nov. 16, 1987

Related U.S. Application Data

[63] Continuation-in-part of Ser. No. 684,661, Dec. 20, 1984, Pat. No. 4,721,619.

[30] Foreign Application Priority Data

Dec. 22, 1983 [IE] Ireland ................... 3057/83

[51] Int. Cl.$^4$ .................. A61K 9/62; A61K 9/16; A61K 9/26
[52] U.S. Cl. ................... 424/461; 424/459; 424/462; 424/470; 424/493; 424/494; 424/495; 424/497
[58] Field of Search ............... 424/461, 462, 489, 474, 424/470, 477, 479, 481, 482, 490, 494, 493, 495, 497

[56] References Cited

U.S. PATENT DOCUMENTS

| | | | |
|---|---|---|---|
| 3,965,255 | 6/1976 | Bloch et al. | 424/472 |
| 4,230,687 | 10/1980 | Sair et al. | 514/965 |
| 4,263,273 | 4/1981 | Appelgren et al. | 424/19 |
| 4,361,546 | 11/1982 | Stricker et al. | 424/462 |
| 4,432,966 | 2/1984 | Zeitoun et al. | 424/471 X |
| 4,496,558 | 1/1985 | DeMarinis et al. | 514/213 |
| 4,499,066 | 2/1985 | Moro et al. | 424/22 |
| 4,555,399 | 11/1985 | Hsiao | 424/80 |
| 4,592,753 | 6/1986 | Panoz | 604/897 |
| 4,600,645 | 7/1986 | Ghebre-Sellassie et al. | 424/19 |
| 4,606,909 | 8/1986 | Bechgaard et al. | 424/482 X |
| 4,609,542 | 9/1986 | Panoz et al. | 424/19 |
| 4,610,870 | 9/1986 | Jain et al. | 424/19 |
| 4,666,702 | 5/1987 | Junginger | 424/497 |
| 4,684,516 | 8/1987 | Bhutani | 424/471 X |
| 4,756,911 | 7/1988 | Drost et al. | 424/472 X |

FOREIGN PATENT DOCUMENTS

| | | | |
|---|---|---|---|
| 0013262 | 7/1980 | European Pat. Off. | |
| 0077956 | 5/1983 | European Pat. Off. | |
| 0173928 | 3/1986 | European Pat. Off. | 424/482 |
| 2313915 | 1/1977 | France | |
| 2039737 | 8/1980 | United Kingdom | 424/19 |

OTHER PUBLICATIONS

Chemical Abstracts, vol. 100, No. 18, Apr. 30, 1984, p. 367, abstract 145016c.

Primary Examiner—Thurman K. Page
Attorney, Agent, or Firm—Marla J. Church; Robert Hardy Falk

[57] ABSTRACT

A diltiazem pellet formulation for oral administration comprises a core of diltiazem or a pharmaceutically acceptable salt thereof in association with an organic acid, and a multi-layer membrane surrounding the core and containing a major proportion of a pharmaceutically acceptable film-forming, water insoluble synthetic polymer and a minor proportion of a pharmaceutically acceptable film-forming, water soluble synthetic polymer. The number of layers in the membrane and the ratio of the water soluble to water insoluble polymer being effective to permit release of diltiazem from the pellet at a rate allowing controlled absorption thereof over a twelve hour period following oral administration. The pellet has a dissolution rate in vitro which when measured in a dissolution apparatus (Paddle) according to U.S. Pharmacopoeia XXI in 0.05 M KCl at pH 7.0 results in not more than 35% of the total diltiazem being released after 2 hours of measurement. Not more than 80% of the total diltiazem is released after six hours of measurement and not less than 85% of the total diltiazem is released after 13 hours of measurement.

20 Claims, 6 Drawing Sheets

DILTIAZEM FORMULATION

BACKGROUND OF THE INVENTION

This invention relates to a controlled absorption pharmaceutical formulation and, in particular, to a controlled absorption form of diltiazem for oral administration.

DESCRIPTION OF THE PRIOR ART

Diltiazem-cis-(+)-3-(acetyloxy)-5-[2-(dimethylamino)ethyl]-2,3-dihydro-2-(4-methoxyphenyl)-1,5-benzothiazepin-4-(5H)-one, is a benzothiazine derivative possessing calcium antagonist activity. Diltiazem blocks the influx of calcium ions in smooth and cardiac muscle and thus exerts potent cardio-vascular effects. Diltiazem has been shown to be useful in alleviating symptoms of chronic heart disease, particularly angina pectoris and myocardial ischemia and hypertension, while displaying a low incidence of side effects. Diltiazem is conventionally administered in tablet form as (30 mg or 60 mg) diltiazem hydrochloride sold under the Trade Mark Cardizem (Marion Laboratories Inc.). Diltiazem in tablet form (30 mg) is also sold under the Trade Mark Herbesser (Tanabe Seiyaku). Diltiazem is also sold in capsule form.

Conventional diltiazem therapy starts with 30 mg administered 4 times daily. The dosage is gradually increased to 240 mg, given in divided doses three or four times daily, at one- to two-day intervals until an optimum response is obtained. Diltiazem is extensively metabolized by the liver and excreted by the kidneys and in bile. According to professional use information issued by Marion Laboratories Inc., Cardizem is absorbed from the known tablet formulation to about 80% and is subject to an extensive first-pass effect, giving an absolute bioavailability, compared to intravenous administration of about 40%. Single oral doses of 30 to 120 mg of Cardizem result in peak plasma levels 2–3 hours after administration. Detectable plasma levels occur within 30–60 minutes after administration, indicating that Cardizem is readily absorbed.

The plasma elimination half-life of diltiazem following single or multiple administration is approximately 3–5 hours. Therapeutic blood levels of Cardizem are thought to be in the range of 50–200 ng/ml.

As stated above, conventional diltiazem capsules and tablets are administered three or four times daily. Such frequent drug administration may reduce patient compliance and produces irregular blood levels; thus adverse therapeutic effects can arise.

An article by McAuley, Bruce J. and Schroeder, John S. in Pharmacotherapy 2: 121, 1982 states that peak plasma levels of diltiazem occur within one hour with normal capsules and within 3 to 4 hours with sustained release tablets.

Co-pending U.S. patent application Ser. No. 684,661, filed Dec. 20, 1984, and incorporated herein by reference, describes and claims an effective diltiazem formulation for twice-daily administration.

The formulation is distinguished by a characteristic dissolution rate when tested under specified conditions, not least its controlled absorption characteristics in vivo, which offer distinct advantages over existing formulations. However, it has been found with certain formulations prepared in accordance with U.S. patent application Ser. No. 684,661, when manufactured in production batches commensurate with commercial scale manufacture to the indicated specifications, that the in vitro performance of the formulation disimproved beyond acceptable limits when stored over the normally required shelf-life periods. This was found to be particularly the case with formulations containing the naturally occurring polymer shellac. Our co-pending patent application No. 121,224, filed simultaneously with the present application describes and claims a stable diltiazem formulation for twice-daily administration which includes naturally occurring polymers such as shellac. However such naturally occurring polymers can exhibit considerable variability in quantity and quality depending on the source and time of collection and accordingly there remains a need to produce alternative formulations which do not require their use.

It is an object of the present invention to provide a controlled absorption diltiazem formulation suitable for twice-daily administration, which is bioequivalent to known oral formulations of diltiazem, which has good stability over normal shelf-life periods of eighteen months to two years, and which contains only synthetic polymeric materials. A further object of the present invention is to improve the method of manufacture of said formulations.

DESCRIPTION OF THE INVENTION

Accordingly, the invention provides a diltiazem pellet formulation for oral administration, said pellet comprising a core of diltiazem or a pharmaceutically acceptable salt thereof in association with an organic acid, the diltiazem component and the organic acid being present in a ratio of from 50:1 to 1:1, and a multi-layer membrane surrounding said core and containing a major proportion of a pharmaceutically acceptable film-forming, water insoluble, synthetic polymer and a minor proportion of a pharmaceutically acceptable film-forming, water soluble synthetic polymer, the number of layers in said membrane and the ratio of said water soluble to water insoluble polymer being effective to permit release of said diltiazem from said pellet at a rate allowing controlled absorption thereof over a twelve hour period following oral administration, said rate being measured in vitro as a dissolution rate of said pellet, which when measured in a dissolution apparatus (paddle) according to U.S. Pharmacopoeia XXI in 0.05M KCl at pH 7.0 substantially corresponds to the following dissolution pattern:

(a) from 5 to 35% of the total diltiazem is released after 2 hours of measurement in said apparatus;

(b) from 55 to 80% of the total diltiazem is released after 6 hours of measurement in said apparatus;

(c) not less than 85% of the total diltiazem is released after 13 hours of measurement in said apparatus.

Preferably, the diltiazem is in the form of a pharmaceutically acceptable salt thereof, more particularly the hydrochloride salt thereof.

The organic acid is preferably represented by one or more of the following acids: adipic acid, ascorbic acid, citric acid, fumaric acid, malic acid, succinic acid or tartaric acid. Especially preferred acids are fumaric acid and succinic acid. The diltiazem component and organic acid are preferably present in a ratio of from 10:1 to 2:1, more especially 6:1 to 3:1.

The core also optionally contains a lubricant which is represented by one or more of the following: sodium stearate, magnesium stearate, stearic acid or talc. The diltiazem and lubricant are preferably present in a ratio of from 0.5:1 to 45:1.

Preferably, the core comprises diltiazem or a pharmaceutically acceptable salt thereof and the associated organic acid and optionally the lubricant embedded in a polymeric material. The diltiazem component and polymeric material are preferably present in a ratio of from 1:1 to 100:1, more particularly from 5:1 to 30:1. The polymeric material may be rapidly soluble in water or, alternatively, may be freely permeable to diltiazem and water.

The term water soluble polymer as used herein includes polymers which are freely permeable to water such as Eudragit RL. Likewise, the term water insoluble polymer as used herein includes polymers which are slightly permeable to water such as Eudragit RS.

The polymeric material preferably consists solely of a water soluble polymer or a polymer which is freely permeable to diltiazem and water. Alternatively, the polymeric material of the core may include a minor proportion of a water insoluble polymer or a polymer which is slightly permeable to diltiazem and water. The ratio of water soluble/freely permeable to water insoluble/slightly permeable polymer is determined by the particular combination of polymers selected. However, in the case of a core including a water soluble polymer and a water insoluble polymer, the ratio of water soluble polymer to water insoluble polymer will normally be in the range of 1:1 to 50:1, more especially 3:1 to 9:1.

The water soluble polymer is suitably polyvinyl alcohol, polyvinylpyrrolidone, methyl cellulose, hydroxypropyl cellulose, hydroxypropylmethyl cellulose, polyethylene glycol or a mixture thereof. An especially preferred water soluble polymer is polyvinylpyrrolidone.

A suitable polymer which is freely permeable to diltiazem and water is a polymer sold under the Trade Mark EUDRAGIT RL.

The water insoluble polymer of the core is preferably selected from ethylcellulose, cellulose acetate, cellulose propionate (lower, medium or higher molecular weight), cellulose acetate propionate, cellulose acetate butyrate, cellulose acetate phthalate, cellulose triacetate, poly(methyl methacrylate), poly(ethyl methacrylate), poly(butyl methacrylate), poly(isobutyl metharylate), poly(hexyl methacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), poly(ethylene), poly(ethylene) low density, poly(ethylene) high density, poly(propylene), poly(ethylene oxide), poly(ethylene terephthalate), poly(vinyl isobutyl ether), poly(vinyl acetate), poly(vinyl chloride) or polyurethane or a mixture thereof.

A suitable polymer which is slightly permeable to diltiazem and water is a polymer sold under the Trade Mark EUDRAGIT RS or a polymer whose permeability is pH dependent and sold under the Trade Mark EUDRAGIT L, EUDRAGIT S or EUDRAGIT E.

EUDRAGIT polymers are polymeric lacquer substances based on acrylates and/or methacrylates.

Polymeric materials sold under the Trade Marks EUDRAGIT RL and EUDRAGIT RS are acrylic resins comprising copolymers of acrylic and methacrylic acid esters with a low content of quaternary ammonium groups and are described in the "EUDRAGIT RL/RS" brochure of Messrs. Rohm Pharma GmbH (1985) wherein detailed physical-chemical data of these products are given. The ammonium groups are present as salts and give rise to the permeability of the lacquer films. EUDRAGIT RL and RS are freely permeable (RL) or slightly permeable (RS), respectively, independent of pH.

EUDRAGIT L is an anionic polymer synthesized from methacrylic acid and methacrylic acid methyl ester. It is insoluble in acids and pure water. It becomes soluble in a neutral to weakly alkaline milieu by forming salts with alkalis. The permeability of EUDRAGIT L is pH dependent. Above pH 5.0, the polymer becomes increasingly permeable. EUDRAGIT L is described in the "EUDRAGIT L" brochure of Messrs. Rohm Pharma GmbH (1986) wherein detailed physical-chemical data of the product are given. EUDRAGIT E and S are also described in the "EUDRAGIT E" and "EUDRAGIT S" brochures of Messrs. Rohm Pharma GmbH (1986).

The core suitably has between 50 and 200 layers of the core-forming materials and is built up in a manner known per se.

Preferably, the multi-layer arrangement of diltiazem, organic acid and polymeric material is built up on a central inert core, suitably consisting of a non-pareil seed of sugar/starch having an average diameter in the range 0.4–0.8 mm, especially 0.5–0.6 mm, in a conventional coating pan. Alternatively, the diltiazem, organic acid and polymeric material may be built up on a central inert core as hereinbefore defined in an automated coating system, for example, a CF granulator.

The core may also include further components to those specified above such as a dispersing agent, a glidant and/or a surfactant.

The diltiazem, organic acid and optional other components are blended to form a homogenous powder. The blend is suitably passed through an appropriate mesh screen, preferably a No. 50 mesh screen, using a milling machine. In the case of coating in a conventional coating pan, alternate layers of a coating solution/suspension of the polymeric material and the powder are applied to the central inert core so as to build up the multi-layer arrangement of the active core.

In accordance with a preferred feature of the present invention the coating solution/suspension of the polymeric material and the powder are applied simultaneously, using an automatic coating system. The coating solution/suspension of the polymeric material comprises one or more polymers dissolved/suspended in a suitable solvent or mixture of solvents. The concentration of the polymeric material in the coating solution/suspension is determined by the viscosity of the final solution/suspension. Preferably, between 10 and 40 parts of inert cores are used relative to the homogenous powder. The addition of a plasticizing agent to the polymeric solution/suspension may be necessary depending on the formulation to improve the elasticity and also the stability of the polymer film and to prevent changes in the polymer permeability over prolonged storage. Such changes could affect the drug release rate. Suitable plasticizing agents include polyethylene glycol, propylene glycol, glycerol, triacetin, dimethyl phthalate, diethyl phthalate, dibutyl phthalate, dibutyl sebacate, triethyl citrate, tributyl citrate, triethyl acetyl citrate, castor oil and varying percentages of acetylated monoglycerides.

Preferred coating materials include:

solutions/suspensions of the polymers cited for use in the application of the powder blend to the central inert core in a suitable organic/aqueous carrier medium.

The membrane of the film-forming polymer or mixture of polymers surrounding the core preferably has a major proportion of a water insoluble polymer and a minor proportion of a water soluble polymer, the ratio of water insoluble to water soluble polymer being determined by the inherent solubility characteristics of the polymers selected.

The membrane may also be composed of a proportion of a polymer which is slightly permeable to diltiazem and water and a proportion of a polymer which is freely permeable to diltiazem and water, the ratio of slightly permeable to freely permeable polymer being determined by the inherent permeability of the respective polymers. The terms "water soluble" and "water insoluble" polymer embrace such polymess as indicated above.

A suitable combination of a polymer which is slightly permeable to diltiazem and water and a polymer which is freely permeable to diltiazem and water is EUDRAGIT RS and EUDRAGIT RL in a ratio of from 1:1 to 50:1, especially 2:1 to 10:1. The membrane may also include a combination of water soluble/water insoluble polymers and polymers which are freely permeable/slightly permeable to diltiazem and water.

The membrane may also comprise a mixture of polymers that are water soluble, freely permeable, water insoluble, slightly permeable and polymers whose permeability/solubility is affected by pH.

Especially suitable polymers for the membrane include:

Polyvinylpyrrolidone, ethylcellulose, Eudragit RL, Eudragit L, Eudragit E, Eudragit S, cellulose acetate and polyvinylalcohol. Commercially available ready-made polymeric solutions/suspensions are also especially preferred. These ready-made solutions/suspensions may optionally contain plasticizing agents to improve the polymer film as described previously. Examples of ready-made solutions/suspensions of polymeric material with or without plasticizing agent include Eudragit RL 30D, Eudragit L 30D, Eudragit E 12.5, Eudragit L 12.5 P, Eudragit E 12.5, Eudragit RL 12.5, Eudragit RS 12.5, (Eudragit being a Trade Mark of Rohm and Haas, whose technical brochures describe the differences between the products), Aquacoat (a Trade Mark of FMC Corporation) and Sure-lease (a Trade Mark of Colorcon Inc.).

The membrane may be built up by applying a plurality of coats of membrane polymer solution or suspension to the core as hereinafter described. The membrane solution or suspension contains the polymer(s) dissolved or suspended, respectively, in a suitable aqueous or organic solvent or mixture of solvents, optionally in the presence of a lubricant. Suitable lubricants are talc, stearic acid, magnesium stearate and sodium stearate. A particularly preferred lubricant is talc. The membrane polymer or mixture of polymers may optionally include a plasticizing agent, the function and choice of which has been previously described.

Preferably, the number of coats of membrane solution or suspension applied is between 20 and 600. The dissolution rate achieved is proportionally slower as the number of membrane coats increases.

The membrane solution or suspension may be applied to the active cores in a conventional coating pan as indicated or, alternatively, using an automated system such as a CF granulator, for example a FREUND CF granulator, a GLATT fluidized bed processor, an AEROMATIC, a modified ACCELA-COTA or any other suitably automated bead coating equipment (FREUND, GLATT, AEROMATIC and ACCELA-COTA are all Trade Marks).

Preferably, 2–25 ml of membrane solution/suspension is applied per coat per kilogram of active cores. In an automated system the total amount of membrane solution/suspension applied to the active cores is the same as that applied in a conventional coating pan, except that the membrane solution/suspension is applied continuously.

Preferably, when a coating pan is used the membrane is applied at a rate of 20–30 coats between each drying step until all of the coats have been applied. Between applications the pellets are dried for between 12 and 18 hours at a temperature of 50°–60° C., most suitably 55° C.

In an automated system a similar number of coats are applied between drying steps. However, the automated system permits such application over a period of only 0.25 to 3 hours, thus permitting much greater efficiencies in production. After each application of this amount of membrane solution/suspension, the pellets are dried at the temperature and for the length of time specified for coating in a coating pan.

In an automated coating system the rate of application of membrane solution/suspension is suitably 0.5–10 g/kg of cores/min. The rate of application of lubricant such as talc is also suitably 0.5–10 g/kg of cores/min.

The pellets may be filled into hard or soft gelatine capsules. The pellets may also be compressed into tablets using a binder and/or hardening agent commonly employed in tabletting such as microcrystalline cellulose sold under the Trade Mark "AVICEL" or a co-crystallised powder of highly modified dextrins (3% by weight) and sucrose sold under the Trade Mark "DI-PAC" in such a way that the specific dissolution rate of the pellets is maintained.

Figure 1:
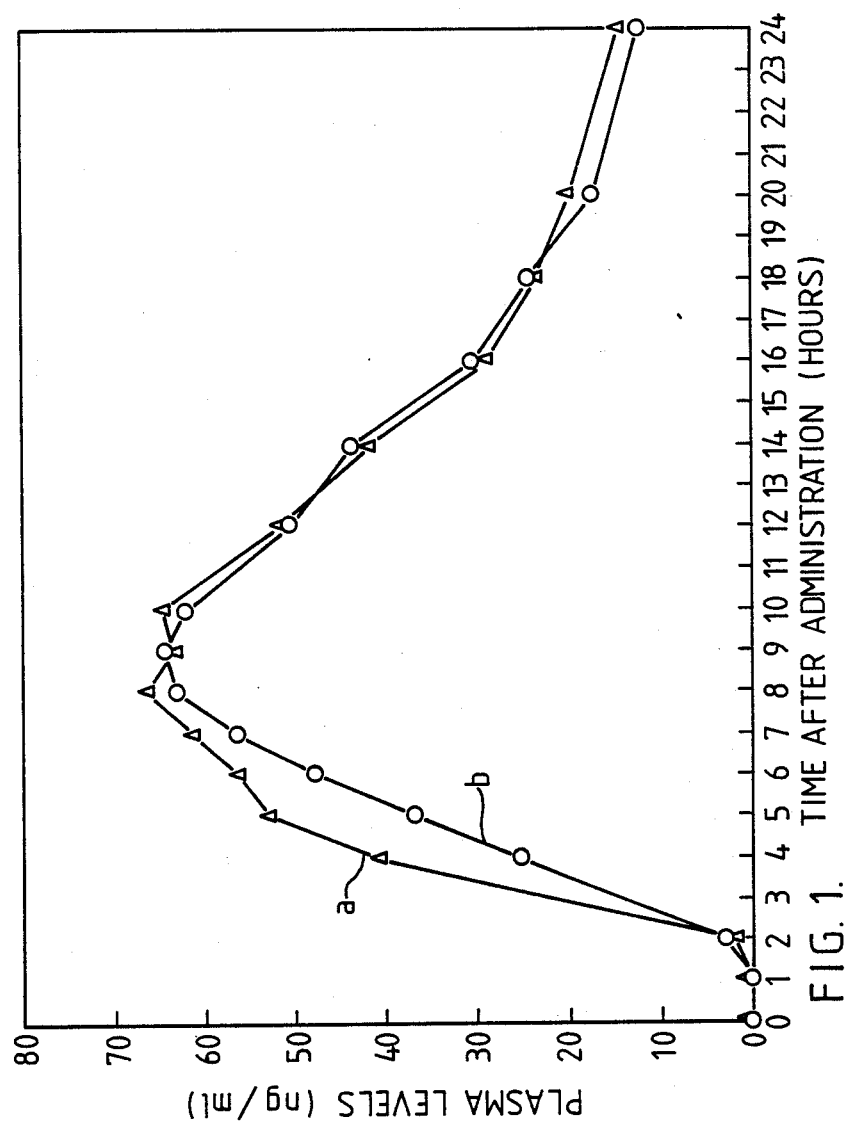
FIG. 1 is a graph of plasma levels (ng/ml) of diltiazem versus time after administration (hours) for the diltiazem formulation prepared in Example 1 (curve a) compared with a diltiazem formulation prepared in accordance with our patent application No. 3057/83 (curve b)

The invention will be further illustrated by the following Examples:

EXAMPLE 1

Diltiazem hydrochloride (10.0 kg), fumaric acid (2.5 kg) and talc (1.0 kg) were blended and milled through a No. 50 mesh screen so as to obtain a homogenous powder.

The powder was applied to starch/sugar seeds (0.6–0.71 mm diameter) (5.0 kg) in a standard coating pan using a coating solution of:

| | |
|---|---|
| 10% Polyvinylpyrrolidone in isopropanol | 75 parts |
| 5% Ethylcellulose in methanol/methylene chloride 50/50 | 20 parts |
| 5% Polyvinylchloride in acetone | 4.5 parts |
| Dibutyl phthalate | 0.1 parts |

The seeds were coated with a measured volume of coating solution followed by dusting on of a measured weight of the powder mix. The coated seeds were allowed to dry and the coating step repeated until all of the powder had been applied. The coated seeds were then dried at 45° C. overnight.

The coated seeds defining the active core of the pellet being prepared were then surrounded by an outer membrane consisting of:

| | |
|---|---|
| 5% Eudragit RS in acetone/isopropanol | 80 parts |
| 5% Eudragit RL in acetone/isopropanol | 15 parts |
| 5% Polyvinylchloride in acetone | 5 parts |
| Talc | 99 parts |
| Dibutyl phthalate | 1 part |

A volume equivalent to 5 ml per kg of coated seeds was applied to the seeds in a standard coating pan. After each coat had been applied the pellets were air dried in the coating pan.

At regular intervals the pellets were placed in an oven and allowed to dry for more than twelve hours.

The pellets were then returned to the coating pan and the process of coating, followed by drying to remove solvents, was continued.

The finished pellets were then subjected to a dissolution test. The dissolution rate of the pellets was tested by the method of U.S. Pharmacopoeia XXI (Paddle Method) in 0.05M KCl adjusted to pH 7.0 and was found to be as follows:

| Time (hours) | Diltiazem hydrochloride % Released |
|---|---|
| 2 | 8.7 |
| 6 | 62.8 |
| 13 | 92.0 |

EXAMPLE 2

Example 1 was repeated except starch/sugar seeds 0.5–0.6 mm were used.

The coating solution used was:

| | |
|---|---|
| 17.5% Polyvinylpyrrolidone in isopropanol | 90 parts |
| 10.0% Cellulose acetate in methylene chloride | 10 parts |

The membrane suspension used was:

| | |
|---|---|
| 12.5% Eudragit RS in acetone/isopropanol | 90 parts |
| 12.5% Eudragit RL in acetone/isopropanol | 10 parts |
| Talc | 100 parts |
| Isopropanol | 100 parts |

At regular intervals the pellets were placed in an oven and dried at 55° C. for more then twelve hours to remove solvents as in Example 1. The dissolution rate was tested according to the U.S. Pharmacopoeia XXI (Paddle Method). The results were as follows:

| Time (hours) | Diltiazem hydrochloride % Released |
|---|---|
| 2 | 28.0 |
| 6 | 69.0 |
| 13 | 94.0 |

EXAMPLE 3

Diltiazem hydrochloride (40 kg), fumaric acid (5 kg) and talc (4.0 kg) were blended and milled through a No. 50 mesh screen so as to obtain a homogenous powder.

The powder so obtained was applied to starch/sugar seeds (20 kg) 0.5–0.6 mm in diameter, in a FREUND CF granulator using a coating solution of:

9.0% Polyvinylpyrrolidone in isopropanol

The seeds were coated with a measured volume of coating solution followed by dusting on of a measured weight of the powder mix. The coated seeds were allowed to dry and the coating step repeated until all of the powder had been applied. The coated seeds were then dried at 55° C. overnight to remove solvent.

The coated seeds defining the active core of the pellet being prepared were then surrounded by an outer membrane. The membrane suspension used was:

| | |
|---|---|
| 12.5% Eudragit RS in acetone/isopropanol | 80 parts |
| 12.5% Eudragit RL in acetone/isopropanol | 20 parts |
| Talc | 100 parts |
| Isopropanol | 100 parts |

The seeds were then coated in a CF granulator with the membrane suspension and dried at regular intervals at 55° C. for 16 hours to remove solvents.

The finished pellets were then subjected to a dissolution test. The dissolution rate of the pellets was tested by the method of U.S. Pharmacopoeia XXI (Paddle Method) in 0.05M KCl adjusted to pH 7.0 and was found to be as follows:

| Time (hours) | Diltiazem hydrochloride % Released |
|---|---|
| 2 | 22.3 |
| 6 | 65.4 |
| 13 | 88.0 |

EXAMPLE 4

Diltiazem hydrochloride (3.0 kg), succinic acid (0.5 kg) and talc (0.3 kg) were blended and milled through a No. 50 mesh screen so as to obtain a homogenous powder.

The powder was applied to starch/sugar seeds (0.6–0.71 mm diameter) (0.75 kg) in a standard coating pan using a coating solution of:

| 9% Polyvinylpyrrolidone in isopropanol | 100 parts |
|---|---|

The active cores of the pellet being prepared were then surrounded by a membrane by applying coats of a suspension consisting of:

| 12.5% EUDRAGIT RS in acetone/isopropanol 40:60 | 20 parts |
|---|---|
| 12.5% EUDRAGIT RL in acetone/isopropanol 40:60 | 20 parts |
| 12.5% EUDRAGIT L in acetone/isopropanol 40:60 | 10 parts |
| Talc | 49 parts |
| Dimethyl phthalate | 1 part |

After each coat had been applied the pellets were air dried in the coating pan. At regular intervals the pellets were placed in an oven and dried at 55° C. for more than twelve hours to remove solvent as in Example 1.

Finished pellets were then subjected to a dissolution test. The dissolution rate of the pellets was tested by the method of the U.S. Pharmacopoeia XXI (Paddle Method) in 0.05M KCl at pH 7.0 at 100 r.p.m.

The dissolution rate was as follows:

| Time (hours) | Diltiazem hydrochloride % Released |
|---|---|
| 2 | 18.9 |
| 6 | 63.4 |
| 13 | 89.6 |

EXAMPLE 5

Diltiazem hydrochloride (40 kg), fumaric acid (10 kg) and talc (4 kg) were blended and milled through a No. 50 mesh screen.

The powder was applied to starch/sugar seeds (0.5–0.6 mm diameter) with a FREUND of granulator using a coating solution of:

| 8% Polyvinylpyrrolidone in ethanol | 90 parts |
|---|---|
| 10% Ethocel (Ethocel is a Trade Mark) in isopropanol | 9.8 parts |
| Diethyl phthalate | 0.2 parts |

A membrane was then applied to the active cores by spraying on a suspension consisting of:

| 12.5% EUDRAGIT RL in acetone/isopropanol 40:60 | 10 parts |
|---|---|
| 12.5% EUDRAGIT RS in acetone/isopropanol 40:60 | 40 parts |
| Isopropanol | 48.75 parts |
| Tributyl citrate | 1.25 parts |

While simultaneously but separately dusting on talc (100 parts by weight) in conventional manner.

A sufficient amount of membrane suspension and talc was applied to achieve a dissolution rate of the pallets, when measured according to U.S. Pharmacopoeia XXI (Paddle Method) as per the previous Examples, as follows:

| Time (hours) | Diltiazem hydrochloride % Released |
|---|---|
| 2 | 24.3 |
| 6 | 71.6 |
| 13 | 98.3 |

EXAMPLE 6

Example 4 was repeated except the application solution consisted of:

| 5% Hydroxypropylmethyl cellulose in methanol/methylene chloride | 99 parts |
|---|---|
| Propylene glycol | 1 part | and the membrane suspension used was

| 10% Cellulose acetate in acetone | 90 parts |
|---|---|
| 5% Polyethylene glycol in acetone | 10 parts |

Talc was added as per Example 4.

A sufficient quantity of membrane suspension was applied to the pellets to achieve the following dissolution rate, all pellets having been dried to remove solvents.

| Time (hours) | Diltiazem hydrochloride % Released |
|---|---|
| 2 | 13.8 |
| 6 | 61.3 |
| 13 | 88.6 |

Pharmacological Data for the Diltiazem Formulation of Example 1

A single-dose crossover study was performed in 6 young healthy male subjects comparing the formulation of Example 1 against the formulation of Example 1 of U.S. patent application Ser. No. 684,661 (hereinafter referred to as Reference). Both the formulation of Example 1 and the Reference formulation were administered as a single encapsulated dose of 120 mg at 0 hours. Plasma concentration of diltiazem was determined at intervals over 24 hours and the results are given in Table 1. Pharmacokinetic data are given in Table 2.

TABLE 1

| MEAN DILTIAZEM PLASMA CONCENTRATIONS (ng/ml) | | |
|---|---|---|
| Time (hours) | Reference | Formulation of Example 1 |
| 0.00 | 0.0 | 0.0 |
| 1.00 | 0.00 | 0.00 |
| 2.00 | 2.75 | 1.87 |
| 4.00 | 25.35 | 40.67 |
| 5.00 | 36.83 | 53.00 |
| 6.00 | 47.67 | 56.33 |
| 7.00 | 56.50 | 61.33 |
| 8.00 | 63.17 | 66.50 |
| 9.00 | 64.33 | 63.50 |
| 10.00 | 62.17 | 64.67 |
| 12.00 | 50.50 | 51.50 |
| 14.00 | 43.50 | 41.67 |
| 16.00 | 30.33 | 29.00 |
| 18.00 | 24.17 | 23.50 |
| 20.00 | 12.42 | 20.07 |

TABLE 1-continued

| MEAN DILTIAZEM PLASMA CONCENTRATIONS (ng/ml) | | |
|---|---|---|
| Time (hours) | Reference | Formulation of Example 1 |
| 24.00 | 12.42 | 14.52 |

TABLE 2

| PHARMACOKINETIC EVALUATION (n = 6) | | |
|---|---|---|
| Parameters | Reference | Formulation of Example 1 |
| AUC (0-∞) | 897.33 | 965.33 |
| F (∞)% | 100 | 111.73 |
| tmax | 9.83 | 8.17 |
| Cmax | 68.50 | 70.50 |
| t½ | 6.43 | 9.13 |

FIG. 1 is a graph of plasma levels (ng/ml) of diltiazem versus time after administration (hours) for a single dose (120 mg) of the diltiazem formulation prepared in Example 1 (curve a) compared with a single dose (120 mg) of the Reference formulation (curve b). As will be appreciated, the data for the Reference formulation was obtained from a different group of subjects to that of present Example 1, thus making any comparison of bioavailability purely indicative. It will be observed from FIG. 1 that a virtually identical absorption pattern is obtained for each formulation, consistent with twice-daily administration. Hence it is submitted the actual bioavailability values would have been similar if the two formulations had been tested in the same subjects.

Pharmacological Data for the Diltiazem Formulation of Example 2

A single-dose crossover study was performed in 6 young healthy male subjects comparing the formulation of Example 2 against the formulation of Example 1 of U.S. patent application Ser. No. 684,661 (hereinafter referred to as Reference). Both formulations were administered as a single 120 mg capsule at 0 hours. Plasma concentration of diltiazem was determined at intervals over 24 hours and the results are given in Table 3. Pharmacokinetic data is given in Table 4.

TABLE 3

| MEAN DILTIAZEM PLASMA CONCENTRATIONS (ng/ml) | | |
|---|---|---|
| Time (hours) | Reference | Formulation of Example 2 |
| 0.00 | 0.0 | 0.0 |
| 1.00 | 0.00 | 0.00 |
| 2.00 | 2.17 | 2.18 |
| 4.00 | 29.67 | 49.50 |
| 5.00 | 52.33 | 68.00 |
| 6.00 | 63.67 | 75.33 |
| 7.00 | 69.00 | 74.17 |
| 8.00 | 69.50 | 67.00 |
| 9.00 | 62.50 | 58.50 |
| 10.00 | 53.83 | 48.50 |
| 12.00 | 38.67 | 35.83 |
| 14.00 | 27.17 | 31.83 |
| 16.00 | 20.17 | 19.83 |
| 18.00 | 15.22 | 15.42 |
| 20.00 | 12.95 | 10.97 |
| 24.00 | 7.70 | 6.53 |

TABLE 4

| PHARMACOKINETIC EVALUATION (n = 6) | | |
|---|---|---|
| Parameters | Reference | Formulation of Example 2 |
| AUC (0-∞) | 769.75 | 793.44 |
| F (∞)% | 100.00 | 110.00 |
| tmax | 7.17 | 6.17 |

TABLE 4-continued

| PHARMACOKINETIC EVALUATION (n = 6) | | |
|---|---|---|
| Parameters | Reference | Formulation of Example 2 |
| Cmax | 76.33 | 81.50 |
| t½ | 5.06 | 4.56 |

Figure 2:
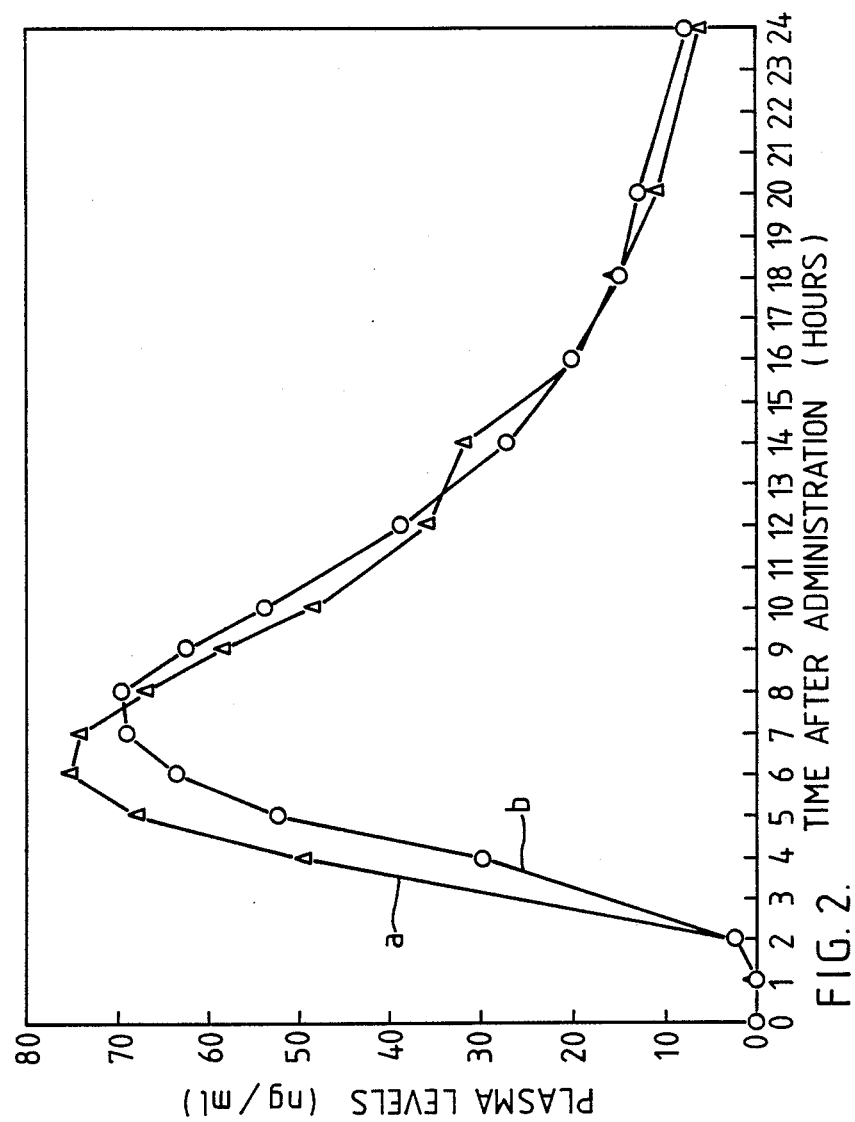
FIG. 2 is a graph of plasma levels (ng/ml) of diltiazem versus time after administration (hours) for the diltiazem formulation prepared in Example 2 (curve a) compared with a diltiazem formulation prepared in accordance with U.S. patent application Ser. No. 684,661 (curve b)

FIG. 2 is a graph of plasma levels (ng/ml) of diltiazem versus time after administration (hours) for a single dose (120 mg) of the diltiazem formulation prepared in Example 2 (curve a) compared with a single dose (120 mg) of the Reference formulation (curve b). As in the case of the pharmacological data for the formulation of Example 1 compared with the Reference, the data for the reference formulation were obtained from a different group of subjects to that of present Example 2, thus making any comparison of bioavailability purely indicative. It will be observed from FIG. 2 that a virtually identical absorption pattern is obtained for each formulation, consistent with twice-daily administration. Hence it is submitted the actual bioavailability values would have been similar if the two formulations had been tested in the same subjects.

Pharmacological Data for the Diltiazem Formulation of Example 3

A steady-state crossover study was performed in 12 young healthy male subjects comparing the formulation of Example 3 against conventional immediate release tablets (Reference tablets).

The formulation of Example 3 was administered as a single 120 mg capsule at 0 and 12 hours (b.i.d.), while the Reference was administered as a single 60 mg tablet at 0, 6, 12 and 18 hours (q.i.d.). Plasma concentration of diltiazem was measured at intervals over 24 hours on Day 5 and the results are given in Table 5. Pharmacokinetic data are given in Table 6.

TABLE 5

| MEAN DILTIAZEM PLASMA CONCENTRATIONS (ng/ml) (Day 5) | | |
|---|---|---|
| Time (hours) | Reference Tablets | Formulation of Example 3 |
| 0.00 | 81.83 | 78.50 |
| 0.50 | 85.50 | — |
| 1.00 | 121.25 | 87.83 |
| 2.00 | 153.42 | 100.75 |
| 3.00 | 166.00 | — |
| 4.00 | 140.17 | 125.42 |
| 6.00 | 90.67 | 118.00 |
| 6.50 | 78.33 | — |
| 7.00 | 96.92 | 109.67 |
| 8.00 | 121.83 | 98.92 |
| 9.00 | 126.33 | 89.92 |
| 10.00 | 103.08 | 82.08 |
| 12.00 | 71.08 | 70.17 |
| 12.50 | 62.17 | — |
| 13.00 | 75.75 | — |
| 14.00 | 88.17 | 70.75 |
| 15.00 | 104.92 | — |
| 16.00 | 99.83 | 83.92 |
| 18.00 | 73.17 | 93.50 |
| 18.50 | 65.25 | — |
| 19.00 | 81.67 | — |
| 20.00 | 103.92 | 98.00 |
| 21.00 | 112.00 | — |
| 22.00 | 108.33 | — |
| 24.00 | 82.00 | 86.00 |

TABLE 6

| | PHARMACOKINETIC EVALUATION (n = 6) | |
|---|---|---|
| Parameters | Reference Tablets | Formulation of Example 3 |
| AUC (0-24 h) | 2474.88 | 2230.33 |
| F (t)% | 100.00 | 90.96 |
| Cmax | 172.08 | 130.42 |
| tmax | 2.75 | 4.17 |

Figure 3:
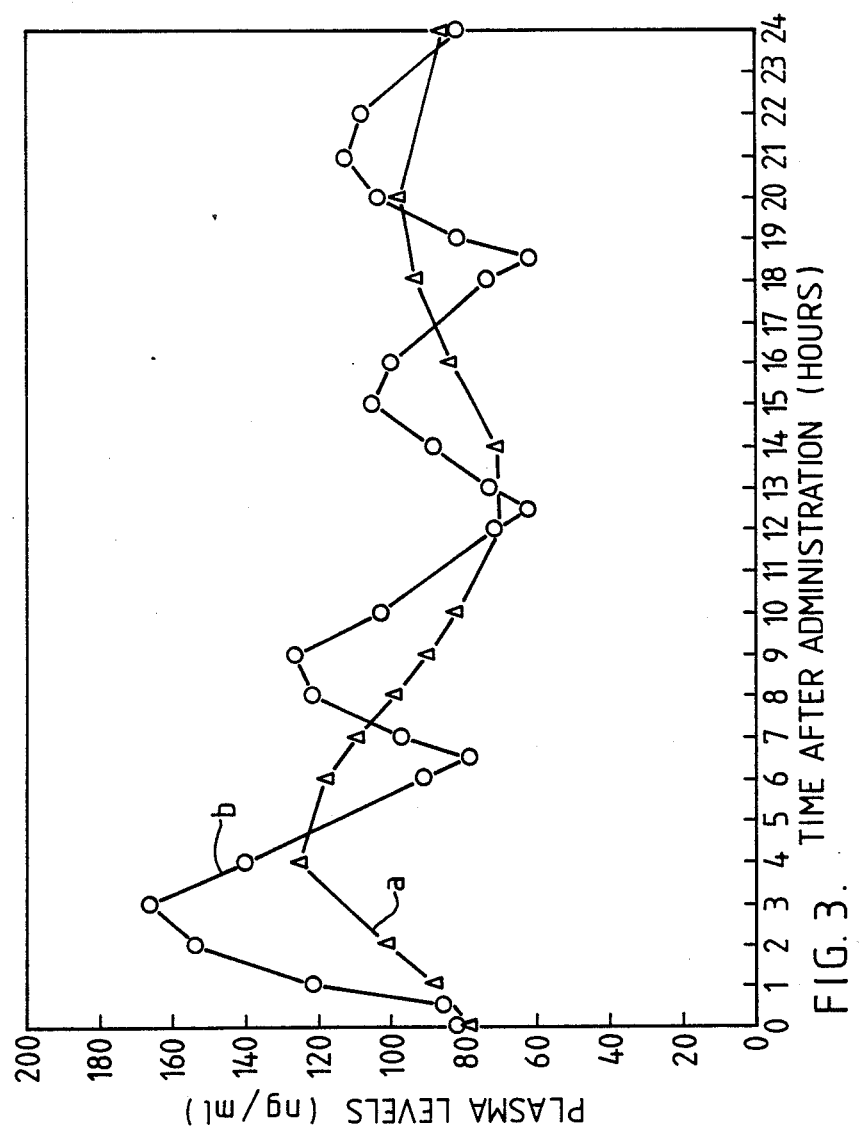
FIG. 3 is a graph of plasma levels (ng/ml) of diltiazem versus time after administration (hours) for the diltiazem formulation prepared in Example 3 (curve a) compared with conventional tablets (curve b)

FIG. 3 is a graph of plasma levels (ng/ml) of diltiazem versus time after administration (hours) for a single dose (120 mg) of the diltiazem formulation prepared in Example 3 (curve a) compared with a single dose (60 mg) of reference tablets administered as indicated above.

It will be observed from the data presented in Table 6 that the formulation of Example 3 is 90.96% bioavailable compared to reference (=100%), and has a quite similar Cmax and AUC (0-24 h). However, the formulation of Example 1 has extended tmax (4.17 hours compared to 2.75 hours for Reference) which satisfies the criteria for controlled absorption orally administered drugs, and further shows a reduction in peak-to-trough fluctuations as indicated in FIG. 3.

Experiments were carried out to assess the stability of the pellet formulation according to the invention relative to formulations of U.S. patent application Ser. No. 684,661.

Figure 4:
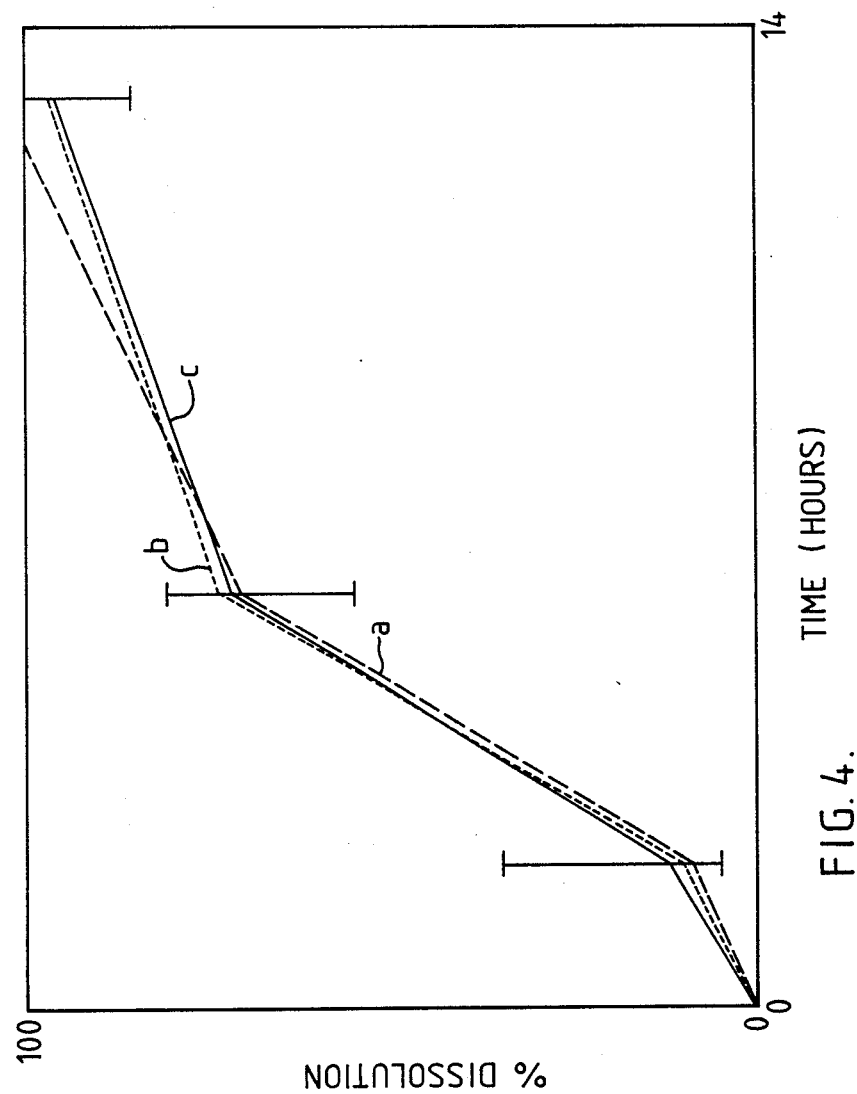
FIG. 4 is a graph of dissolution (%) versus time (hours) of a batch of pellets prepared in accordance with Example 3, stored under ambient conditions as hereinafter described, and tested at different times after manufacture.

Dissolution tests of the type described in Example 1 were carried out on a batch of the pellet formulation of Example 3 after storage in ambient conditions over a period concomitant with commercial shelf-life, in accordance with established criteria. The results are presented in FIG. 4 which is a graph of dissolution (%) versus time (hours) taken at three different time points after manufacture of the formulation of Example 3 under the indicated conditions and is indicative of the stability of the formulation under these conditions. In FIG. 4 curve a represents the batch as tested after 3 months of storage, curve b the batch as tested after 6 months of storage and curve c the batch as tested after 18 months of storage.

Figure 5:
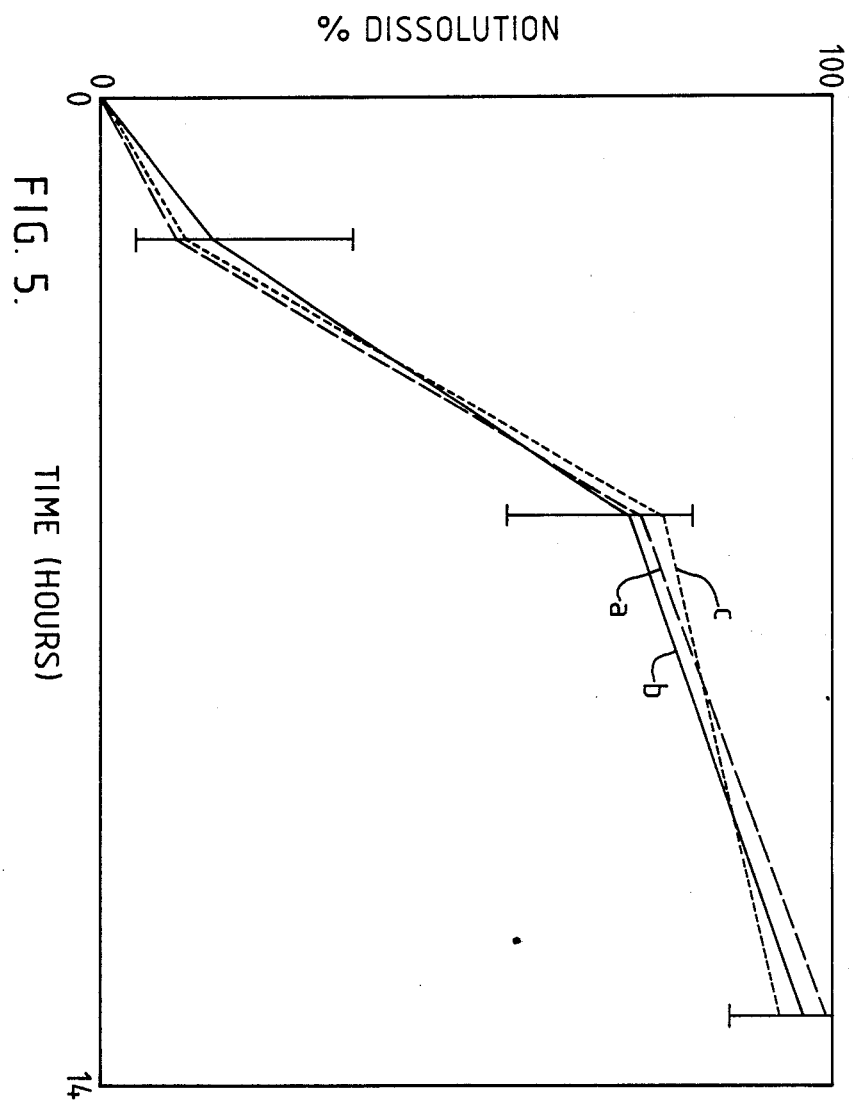
FIG. 5 is a graph of dissolution (%) versus time (hours) of a batch of pellets prepared in accordance with Example 3, 'stored' under accelerated conditions as hereinafter described and tested at different times after manufacture.

Dissolution tests of the type described in Example 1 were also carried out on a batch of the pellet formulation of Example 3 under 'accelerated conditions' (37° C. and 75% relative humidity) in accordance with established criteria. The results are presented in FIG. 5 which is a graph of dissolution (%) versus time (hours) taken at three different time points after the manufacture of the formulation of Example 3 under the indicated conditions and is indicative of the stability of the formulation under these conditions. In FIG. 5 curve a represents the batch as tested after 1 month of storage, curve b the batch as tested after 3 months of storage and curve c the batch as tested after 6 months of storage.

Figure 6:
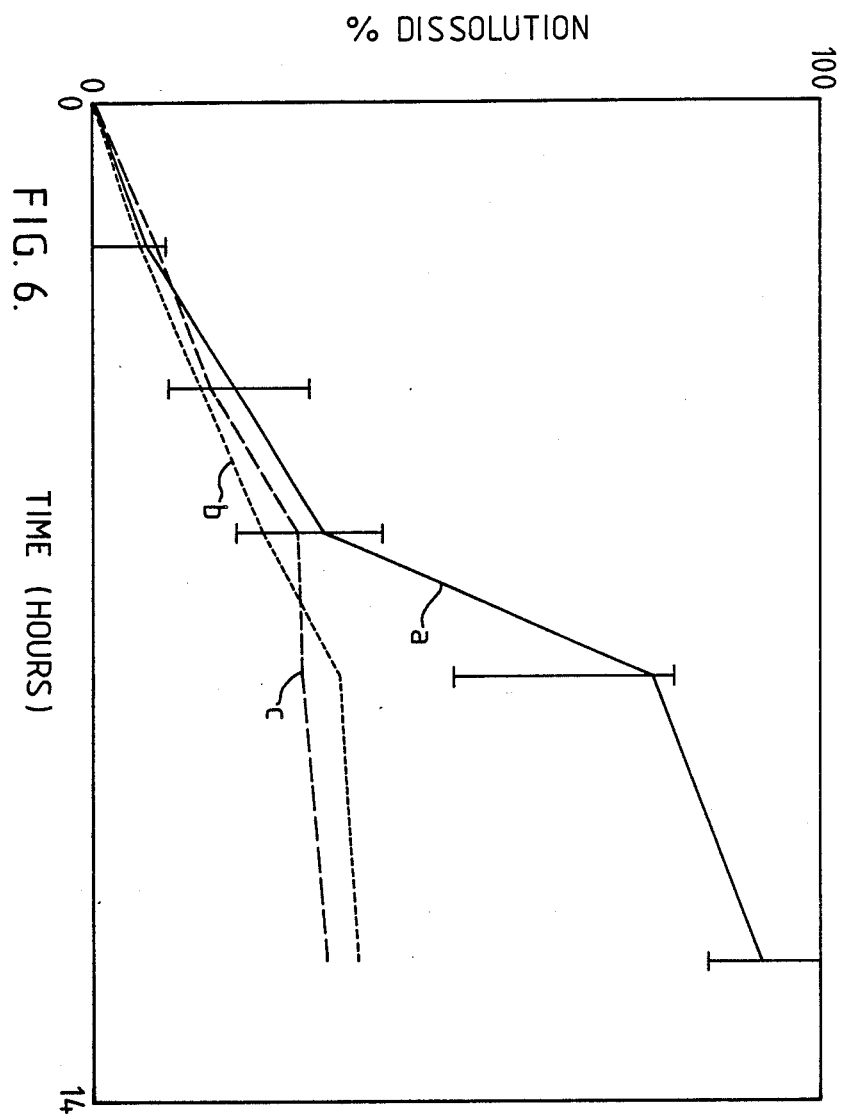
FIG. 6 is a graph of dissolution (%) versus time (hours) of a batch of pellets prepared in accordance with Example 1 of U.S. patent application Ser. No. 684,661, 'stored' under accelerated conditions as hereinafter described, and tested at different times after manufacture.

Identical dissolution tests under identical accelerated conditions were carried out on a batch of a pellet formulation prepared in accordance with Example 1 of U.S. patent application Ser. No. 684,661. The results are presented in FIG. 6 which again is a graph of dissolution (%) versus time (hours) taken at three different time points after the manufacture of the formulation in question. In FIG. 6 curve a represents the batch as tested after 1 month of storage, curve b the batch as tested after 3 months of storage and curve c the batch as tested after 6 months of storage. A comparison of FIGS. 4, 5 and 6 demonstrates the stability of the formulation of the present invention relative to the formulation of U.S. patent application Ser. No. 684,661 as indicated by the error bars which represent the dissolution specifications for each of the formulations. As will be observed the formulation of U.S. patent application Ser. No. 684,661 under the specified conditions is unstable and therefore if commercially used would require excessive inventory control procedures.

The formulation according to the invention, which is characterised by a specific in vitro dissolution rate and a more controlled manufacturing process, has excellent stability over the normal marketing shelf-life (18 months to 2 years) in terms of both in vivo and in vitro performance.

What we claim is:

1. A diltiazem pellet formulation for oral administration, said pellet comprising a core of diltiazem or a pharmaceutically acceptable salt thereof in association with an organic acid, the diltiazem component and the organic acid being present in a ratio of from 50:1 to 1:1, and a multi-layer membrane surrounding said core and containing a major proportion of a pharmaceutically acceptable film-forming, water insoluble synthetic polymer and a minor proportion of a pharmaceutically acceptable film-forming, water soluble synthetic polymer, the number of layers in said membrane and the ratio of said water soluble to water insoluble polymer being effective to permit release of said diltiazem from said pellet at a rate allowing controlled absorption thereof over a twelve hour period following oral administration, said rate being measured in vitro as a dissolution rate of said pellet, which when measured in a dissolution apparatus (paddle) according to U.S. Pharmacopoeia XXI in 0.05M KCl at pH 7.0 substantially corresponds to the following dissolution pattern:
    (a) from 5 to 35% of the total diltiazem is released after 2 hours of measurement in said apparatus;
    (b) from 55 to 80% of the total diltiazem is released after 6 hours of measurement in said apparatus;
    (c) not less than 85% of the total diltiazem is released after 13 hours of measurement in said apparatus.

2. A pellet formulation according to claim 1, wherein the diltiazem or pharmaceutically acceptable salt thereof and organic acid are present in a ratio of from 10:1 to 2:1.

3. A pellet formulation according to claim 1 wherein the core comprises:
    (a) a powder mixture containing diltiazem or a pharmaceutically acceptable salt thereof, an organic acid selected from the group consisting of adipic acid, ascorbic acid, citric acid, fumaric acid, malic acid, succinic acid and tartaric acid, and
    (b) a polymeric material containing a major proportion of a pharmaceutically acceptable water soluble synthetic polymer and a minor proportion of a pharmaceutically acceptable water insoluble synthetic polymer, said core comprising layers of said powder mixture and said polymeric material superimposed one upon the other and said polymeric material being present in an amount effective to ensure that all of said powder mixture is coated into said core.

4. A pellet formulation according to claim 1, wherein the water soluble polymer in the core or membrane is the same or different and is selected from the group consisting of polyvinyl alcohol, polyvinylpyrrolidone, methyl cellulose, hydroxypropyl cellulose, hydroxypropylmethyl cellulose and polyethylene glycol or a mixture thereof.

5. A pellet formulation according to claim 1, wherein the water soluble polymer in the core or membrane is replaced by a polymeric material which is freely permeable to diltiazem and water and comprises a copolymer of acrylic and methacrylic acid esters.

6. A pellet formulation according to claim 1, wherein the water insoluble polymer in the core is selected from the group consisting of ethylcellulose, cellulose acetate, cellulose propionate (lower, medium or higher molecular weight), cellulose acetate propionate, cellulose acetate butyrate, cellulose acetate phthalate, cellulose triacetate, poly(methyl methacrylate), poly(ethyl methacrylate), poly(butyl methacrylate), poly(isobutyl methacrylate), poly(hexyl methacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), poly(ethylene), poly(ethylene) low density, poly(ethylene) high density, poly(propylene), poly(ethylene oxide), poly(ethylene terephthalate), poly(vinyl isobutyl ether), poly(vinyl acetate), poly(vinyl chloride) and polyurethane or a mixture thereof.

7. A pellet formulation according to claim 3, wherein the water insoluble polymer in the core is replaced by a polymeric material which is slightly permeable to diltiazem and water and comprises a copolymer of acrylic and methacrylic acid esters.

8. A pellet formulation according to claim 3, wherein the diltiazem, organic acid and polymeric material are built up on an inert core.

9. A pellet formulation according to claim 8, wherein the inert core is a non-pareil seed of sugar/starch having an average diameter in the range 0.4–0.8 mm.

10. A pellet formulation according to claim 1, wherein the core includes one or more additional components selected from the group consisting of a dispersing agent, a glidant and a surfactant.

11. A pellet formulation according to claim 1, which includes a plasticizing agent selected from the group consisting of polyethylene glycol, propylene glycol, glycerol, triacetin, dimethyl phthalate, diethyl phthalate, dibutyl phthalate, dibutyl sebacate, triethyl citrate, tributyl citrate, triethyl acetyl citrate, castor oil and an acetylated monoglyceride.

12. A pellet formulation according to claim 1, which contains diltiazem hydrochloride as the active ingredient.

13. A process for the production of a pellet formulation according to claim 1, which comprises forming a core of diltiazem or a pharmautically acceptable salt thereof and an organic acid and enclosing the core in a membrane of a film-forming polymer or mixture thereof as defined in claim 1 which permits release of the diltiazem or the pharmaceutically acceptable salt thereof in the manner set out in claim 1.

14. A capsule or tablet comprising a formulation of pellets according to claim 1.

15. A pellet formulation according to claim 2, wherein the core comprises:
  (a) a powder mixture containing diltiazem or a pharmaceutically acceptable salt thereof, an organic acid selected from the group consisting of adipic acid, ascorbic acid, citric acid, fumaric acid, malic acid, succinic acid and tartaric acid, and
  (b) a polymeric material containing a major proportion of a pharmaceutically acceptable water soluble synthetic polymer and a minor proportion of a pharmaceutically acceptable water insoluble synthetic polymer, said core comprising layers of said powder mixture and said polymeric material superimposed one upon the other and said polymeric material being present in an amount effective to ensure that all of said powder mixture is coated into said core.

16. A pellet formulation according to claim 2, wherein the core includes one or more additional components selected from the group consisting of a dispersing agent, a glidant and a surfactant.

17. A pellet formulation according to claim 3, wherein the core includes one or more additional components selected from the group consisting of a dispersing agent, a glidant and a surfactant.

18. A pellet formulation according to claim 15, wherein the core includes one or more additional components selected from the group consisting of a dispersing agent, a glidant and a surfactant.

19. A diltiazem pellet formulation for oral administration, said pellet comprising a core of diltiazem or a pharmaceutically acceptable salt thereof in association with an organic acid, the diltiazem component and the organic acid being present in a ratio of from 50:1 to 1:1, and a membrane surrounding said core comprising a multiplicity of sequentially applied and dried layers, each layer containing a major proportion of a pharmaceutically acceptable film-forming, water insoluble synthetic polymer and a minor proportion of a pharmaceutically acceptable film-forming, water soluble synthetic polymer, the number of layers in said membrane and the ratio of said water soluble to water insoluble polymer being effective to permit release of said diltiazem from said pellet at a rate allowing controlled absorption thereof over a twelve hour period following oral administration.

20. A formulation as claimed in claim 19, wherein said membrane comprises from 20 to 600 layers and the in vitro dissolution rate of said pellet, when measured in a dissolution apparatus (paddle) according to U.S. Pharmacopoeia XXI in 0.05M KCl at pH 7.0, substantially corresponds to the following dissolution pattern:
  (a) from 5 to 35% of the total diltiazem is released after 2 hours of measurement in said apparatus;
  (b) from 55 to 80% of the total diltiazem is released after 6 hours of measurement in said apparatus; and
  (c) not less than 85% of the total diltiazem is released after 13 hours of measurement in said apparatus.

* * * * *